(12) United States Patent
Appenzeller et al.

(10) Patent No.: US 9,642,662 B2
(45) Date of Patent: May 9, 2017

(54) LOCKING SPIRAL ANCHORING SYSTEM

(75) Inventors: Andreas Appenzeller, Biel (CH); Robert Frigg, Bettlach (CH); Tom Overes, Langendorf (CH); Nicolas Bouduban, Bruegg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1805 days.

(21) Appl. No.: 12/752,748

(22) Filed: Apr. 1, 2010

(65) Prior Publication Data

US 2010/0256690 A1  Oct. 7, 2010

Related U.S. Application Data

(60) Provisional application No. 61/166,039, filed on Apr. 2, 2009.

(51) Int. Cl.
*A61B 17/86* (2006.01)
*A61B 17/80* (2006.01)

(52) U.S. Cl.
CPC ........ *A61B 17/869* (2013.01); *A61B 17/8057* (2013.01); *A61B 17/8685* (2013.01)

(58) Field of Classification Search
CPC .................................... A61B 17/869
USPC ........... 606/286, 297, 300–321; 411/16, 251, 411/421
See application file for complete search history.

(56) References Cited

U.S. PATENT DOCUMENTS

| | | | |
|---|---|---|---|
| 4,738,062 A | 4/1988 | Dickey | |
| 4,762,453 A | 8/1988 | DeCaro | |
| 4,917,554 A | 4/1990 | Bronn | |
| 5,662,683 A | 9/1997 | Kay | |
| 5,728,116 A | 3/1998 | Rosenman | |
| 6,174,312 B1 | 1/2001 | Laminger | |
| 6,551,322 B1 | 4/2003 | Lieberman | |
| 6,656,184 B1 | 12/2003 | White et al. | |
| 6,951,561 B2 | 10/2005 | Warren et al. | |
| 6,953,462 B2* | 10/2005 | Lieberman | 606/325 |
| 7,144,413 B2 | 12/2006 | Wilford et al. | |
| 7,189,251 B2 | 3/2007 | Kay | |
| 2002/0055739 A1* | 5/2002 | Lieberman | 606/61 |
| 2002/0055742 A1 | 5/2002 | Lieberman | |
| 2003/0083663 A1 | 5/2003 | Goldhahn et al. | |
| 2004/0073216 A1 | 4/2004 | Lieberman | |
| 2004/0078084 A1 | 4/2004 | Albertorio | |
| 2004/0082953 A1 | 4/2004 | Petit | |
| 2004/0172031 A1* | 9/2004 | Rubecamp et al. | 606/73 |
| 2006/0009771 A1* | 1/2006 | Orbay et al. | 606/69 |

(Continued)

FOREIGN PATENT DOCUMENTS

| | | |
|---|---|---|
| EP | 0 374 088 | 6/1990 |
| JP | 07-222752 | 8/1995 |
| SU | 1071297 | 2/1984 |

(Continued)

*Primary Examiner* — Andrew Yang (74) *Attorney, Agent, or Firm* — Fay Kaplun & Marcin, LLP (57) ABSTRACT

A bone fixation screw comprises a proximal head being configured to lockingly engage a bone plate hole and a substantially helical shaft extending distally from the head along a substantially helical path. The head and the shaft are rotatably coupled to each other so that the shaft can rotate about a central longitudinal axis thereof with respect to the head.

17 Claims, 10 Drawing Sheets

(56) References Cited

U.S. PATENT DOCUMENTS

2006/0129147 A1   6/2006  Biedermann et al.
2006/0276895 A1  12/2006  Pellegrino et al.

FOREIGN PATENT DOCUMENTS

WO        01/76488     10/2001
WO      2008/021656     2/2008

* cited by examiner

LOCKING SPIRAL ANCHORING SYSTEM

PRIORITY CLAIM

This application claims priority to U.S. Provisional Application Ser. No. 61/166,039 entitled "Locking Spiral Anchoring Means" filed on Apr. 2, 2009 to Andreas Appenzeller, Robert Frigg, Tom Overes and Nicolas Bouduban, the entire disclosure of which is incorporated herein by reference.

BACKGROUND INFORMATION

Osteoporotic bone fractures are often treated with fixation elements such as screws or pins to stabilize fractured portions of the bone. Such fixation elements secure a bone plate to the bone to aid in both internal and external stabilization thereof. Presently available bone fixation screws include locking head screws, LCP screws and BORIS rivet screws, which splay radially outward within the target portion of the bone. However, these bone fixation screws are often insufficient to prevent further fracture collapse due to one or more of improper fixation, insufficient anchoring strength and bone degradation such as that caused by osteoporosis.

SUMMARY OF THE INVENTION

The present invention is directed to a system for bone fixation which includes a proximal head being configured to lockingly engage a bone plate hole and a substantially helical shaft extending distally from the head along a substantially helical path. The head and the shaft are rotatably coupled to each other so that the shaft can rotate about a central longitudinal axis thereof with respect to the head.

DETAILED DESCRIPTION

The present invention may be further understood with reference to the following description and the appended drawings. The present invention relates generally to devices and methods for the fixation of osteoporotic fractures. It is noted that although embodiments of the invention are described in regard to the treatment of fractures of long bones, the present invention may also be employed in maxillofacial bone fixation procedures, spinal fixation procedures or any other bone fixation procedure. The present invention relates to a bone screw and a bone locking apparatus wherein the bone screw comprises a shaft having the shape of a helix formed with a helically wound thin rod to effectively engage bone segments in a manner minimizing the possibility of further collapse of the bone and provides an efficient holding pressure by increasing the effective screw diameter. Additionally, the helical shape acts like a spring, providing a physician or other user of the device with tactile feedback to avoid the risk of penetrating a joint surface of a target bone. The helical bone locking apparatus of the present invention further permits the intersection of multiple bone locking spirals within a bone. Specifically, the spiral shape of the bone locking apparatus permits the intersection of multiple bone locking apparatuses along intersecting axes which would not be possible with conventional screws as the solid cylinder-like shafts of the conventional screws would interfere within one another. The invention increases therefore the options for placement of fixation elements available to the physician. Thus the present invention permits the application of bone plates formed with plate hole axes which intersect within the bone in a manner unsuitable for bone plates designed to receive straight shaft bone fixation elements. Those skilled in the art will understand that, as used in this application, the term proximal refers to a direction approaching a physician or other user of the device of the present invention while the term distal refers to a direction approaching a target bone into which the bone spiral is to be inserted—i.e., away from the physician or other user.

Bone screws known in the art and exhibiting two different threads of considerably different pitch (e.g., interference screws) are generally unsuitable when used together with bone plates having threaded plate holes for receiving the outer thread of the bone screw head. Specifically, locking of the bone screw head in the inner thread of the bone plate hole requires approximately two full 360° turns which turning may cause a shaft of the bone screw to drill a hole into bone, resulting in loss of fixation. The freedom of the shafts of the fixation elements of the present invention to rotate relative to their heads while remaining axially connected allows the insertion of these elements despite differences in pitch between the head and shaft without causing this drilling effect. Furthermore, the bone screw according to the present invention may be formed with a smooth conical head to permit insertion into a corresponding smooth conical bone plate hole, thus locking the head to the bone plate hole immediately upon contact without the need for further rotation of the screw head in the bone plate hole.

Figure 1:
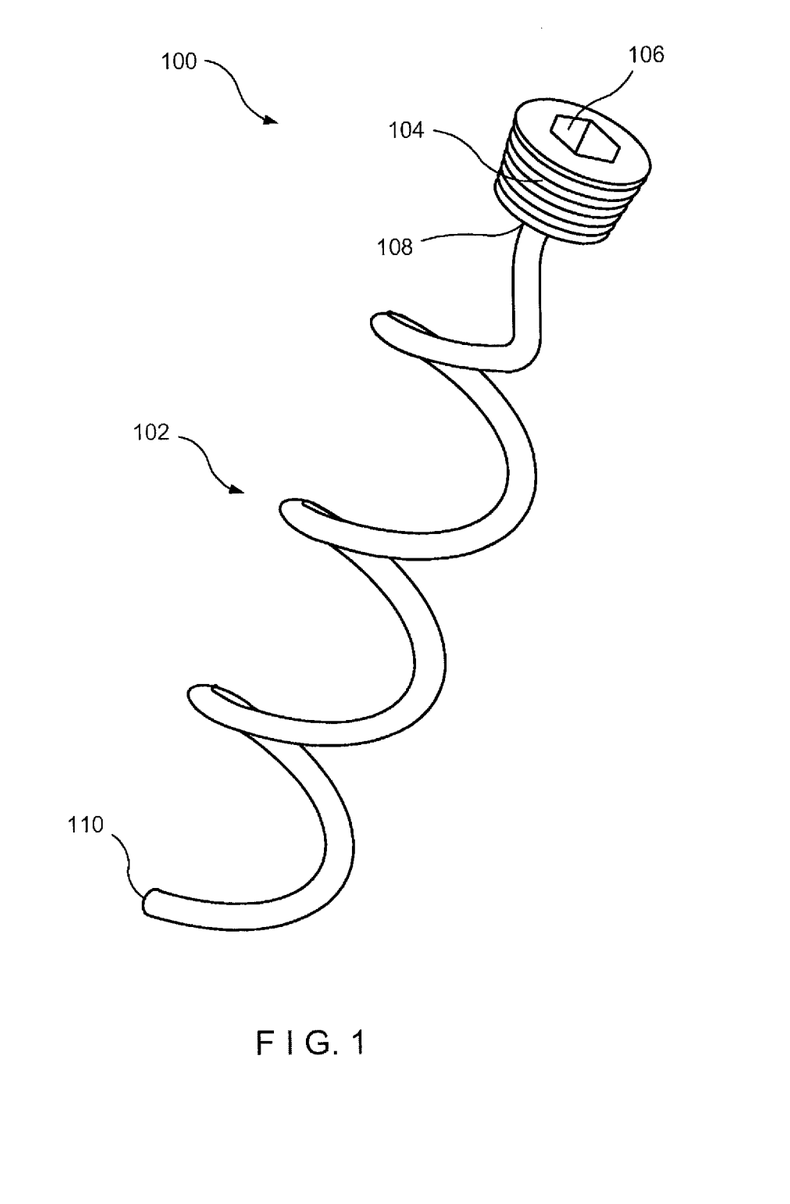
FIG. 1 shows a perspective view of a bone locking spiral according to a first exemplary embodiment of the present invention.

As shown in FIG. 1, a bone screw 100 according to a first embodiment of the present invention comprises a first shaft 102 having a proximal head 104 sized and shaped to engage a driver (not shown) to permit manipulation thereof. Specifically, the head 104 is formed with an engaging structure such as, for example, a hexagonal recess 106 configured for engagement with a hexagonal driver for transmission of torque, as those skilled in the art will understand. It is noted however, that the recess 106 in the head 104 may comprise any shape known in the art including, but not limited to a slotted drive, a hex drive, a star shaped torque drive and a square drive with a shape of the selected driver (not shown) being chosen to accommodate the head 104. An outer wall of the head 104 has a conical shape to permit locking engagement with a correspondingly conical opening in a bone plate, as will be described in greater detail hereinafter. The first shaft 102 extends from a proximal end 108 attached to the head 104 along a helical path to a distal end 110. The first shaft 102 is formed of a material exhibiting a degree of rigidity required to permits its insertion through a target portion of bone including, but not limited to, steel, titanium and Polyetheretherketone ("PEEK"). In one embodiment, the distal end 110 may be sharpened to facilitate insertion into, for example, hard bone. It is noted, however, that a pointed distal tip 110 is not required and may be omitted as needed, such as when inserting the first shaft 102 into porotic bone, as those skilled in the art will understand. In an exemplary embodiment, the first shaft 102 is formed by a helically wound thin rod as a solid element without any openings or channels extending therethrough and has a substantially circular cross-section. It is noted, however, that the first shaft 102 may comprise any cross-sectional shape known in the art without deviating from the spirit and scope of the present invention, including, but not limited to, oval, triangular, rectangular, hexagonal, etc.

A pitch of the first shaft 102 may be selected to facilitate insertion into the bone while promoting bone ingrowth therearound, as those skilled in the art will understand. In an exemplary embodiment, a pitch of the first shaft 102 may be approximately 3-10 mm. It is noted however, that the pitch may be modified to any value to accommodate requirements for a particular procedure, including bone size and bone density, wherein the selected helical pitch affects a holding strength of the first shaft 102 relative to the bone. Additionally, as shown in FIG. 1, an outer diameter of selected turns of the first shaft 102 may be greater than an outer diameter of a head 104 of the first shaft 102. This increased diameter increases the contact area for the first shaft 102 increasing a holding strength thereof. Accordingly, an outer diameter of any number of turns of the first shaft 102 may be increased or decreased to conform to the requirements of a particular procedure. If more than one bone screws 100 are to be inserted into a bone plate the outer diameter of the head 104 is preferably equal or greater than the outer diameter of a virtual cylinder enveloping the first shaft 102.

Figure 5:
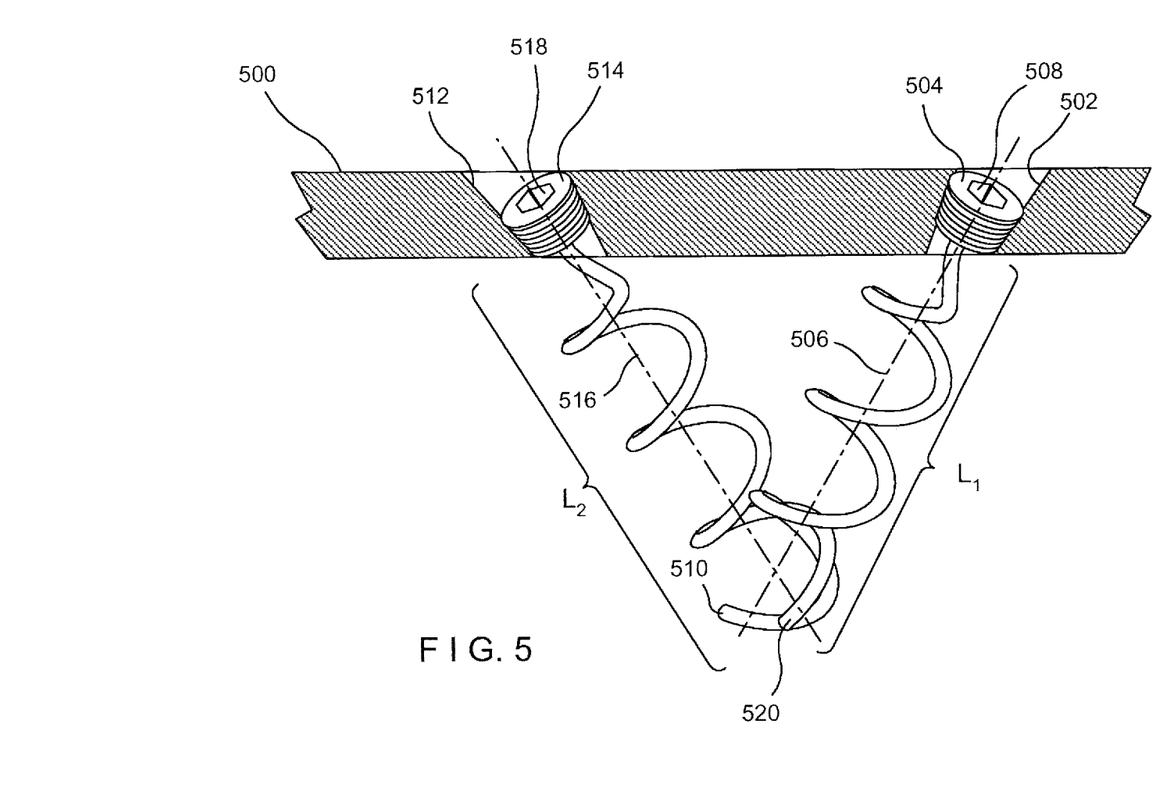
FIG. 5 shows a partial cross-sectional view of a first exemplary bone plate for use with the bone locking spiral of the present invention.

In accordance with a first exemplary method of the present invention, a bone plate such as the bone plate 500 of FIG. 5 is first positioned over a target portion of a fractured bone (not shown) in accordance with standard bone fixation procedures. The bone plate 500 comprises at least one first plate hole 502 extending through the plate 500 from a top surface which, when placed on a bone in a desired orientation, faces away from the bone, to a bottom surface which, in the desired orientation, faces the bone and a second plate hole 512 extending through the plate 500 adjacent to the first plate hole 502. It is noted that although the first and second plate holes 502, 512 are shown to extend at angles that are offset from a normal axis of the bone plate 500 the holes can be formed with any angles without deviating from the scope of the present invention. The first plate hole 502 and second plate hole 512 each define respective first and second hole axes 506, 516 that are configured to intersect one another at a predetermined distance below a bottom surface of the bone plate 500. As mentioned above and described in greater detail below, an exemplary embodiment of the present invention permits the intersection of multiple bone spirals at a point within the bone. Unlike conventional bone screws, a first shaft 504 according to the present invention comprises a single coil defining multiple turns separated from one another by a predetermined space through which another bone spiral or any other appropriately sized bone fixation device may pass. Thus, whereas conventional straight bone fixation devices such as bone screws cannot be inserted over axes which intersect one another within the length of the fixation devices, the first shaft 504 according to the present invention permits the intertwining intersection of a first bone spiral with another bone spiral or with any other bone fixation device. Specifically, if conventional bone screws were to be employed with the bone plate 500, engagement of distal portions of each of the bone screws would prevent the full insertion thereof into the bone plate 500. In the plate 500 according to the present embodiment, however, there is no such limitation on the placement and orientation of the plate holes providing a greater freedom in selecting the angles and positions of insertion of bone fixation elements through the plate 500.

Once the bone plate 500 has been positioned as desired over the bone, the first shaft 504 is inserted through the first plate hole 502. Torque applied by a driver (not shown) to the first shaft 504 causes a spiraling insertion thereof into the target bone. The first shaft 504 is screwed into the bone until a head 508 thereof lockingly engages the first plate hole 502. The head 508 is configured to lockingly engage the first plate hole 502 to prevent the head 508 from further rotating relative to the bone plate 500. Specifically, the conical shape of the first plate hole 502 is sized and shaped to receive the conical head 508 by a frictional lock, as those skilled in the art will understand. In the locked configuration, a distal end 510 of the first shaft 504 extends into the bone by a first length $L_1$ along the first hole axis 506. A second bone fixation device such as a second shaft 514 is then inserted into the second plate hole 512. It is noted that although the second shaft 514 is another helically wound shaft as shown in the present embodiment, the second bone fixation device can be another device known in the art (e.g., a conventional straight bone pin or screw). The second shaft 514 is screwed into the bone along the second plate hole axis 516. The second shaft 514 is sized such that, when inserted into the bone along the second plate hole axis 516, the second bone spiral 514 protrudes into the bone by a length $L_2$ sufficient to permit a distal end 520 thereof to intersect a distal portion of the first shaft 504, as shown in FIG. 5. Specifically, a shape of the second shaft 514 permits a distal portion thereof to wind around a portion of the first shaft 504, thus causing an intertwining engagement therebetween. A conical head 518 of the second shaft 504 is then tightened into the second conical plate hole 512 by a frictional lock.

Figure 2:
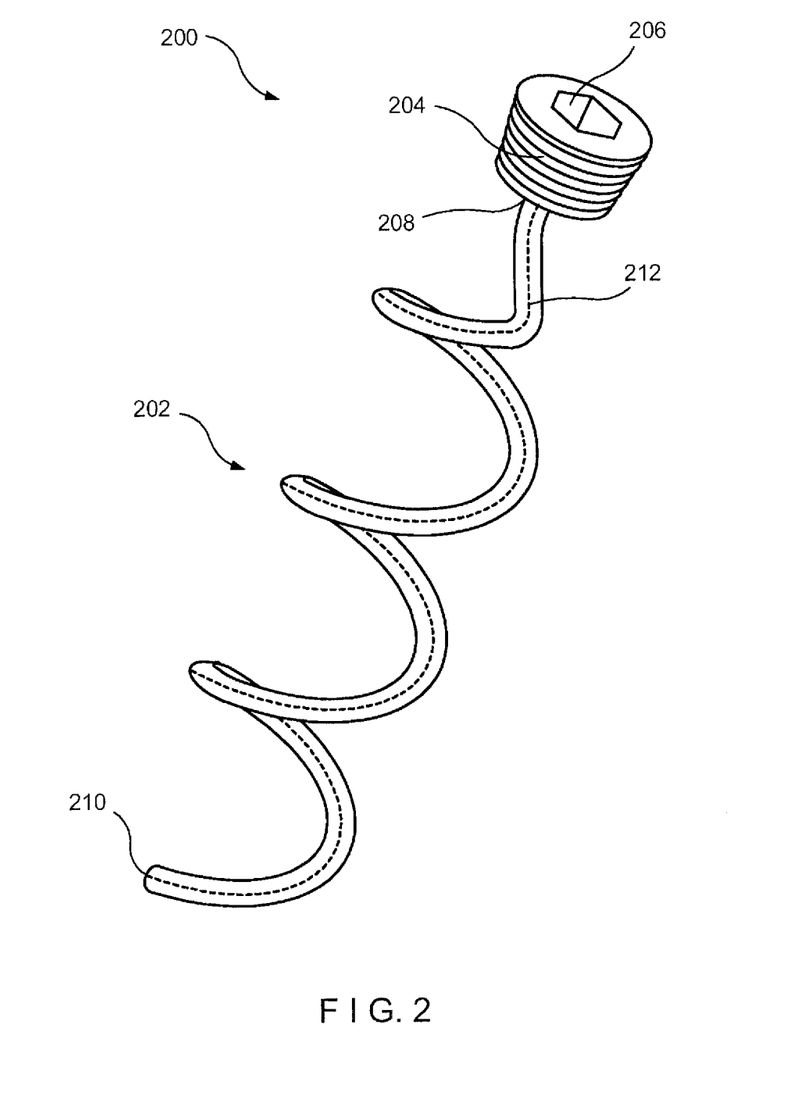
FIG. 2 shows a perspective view of a bone locking spiral according to a second exemplary embodiment of the present invention.

As shown in FIG. 2, a bone screw 200 according to an alternate embodiment of the present invention comprises a first shaft 202 formed substantially similarly to the first shaft 102 with the exception of a lumen 212 extending therethrough. The lumen 212 is open at both a proximal end 208 adjacent a head 204 and at a distal end 210 and is sized and shaped to permit injection of a strengthening material (e.g., cement) therethrough into a target portion of the bone to aid in bone fixation, to strengthen a bond between the first shaft 202 and the bone, to avoid a secondary loss of reduction due to implant cut-out and to reduce joint sintering, as those skilled in the art will understand. The lumen 212 may have a circular cross-sectional shape or, alternatively, may be formed with any shape known in the art.

Figure 3:
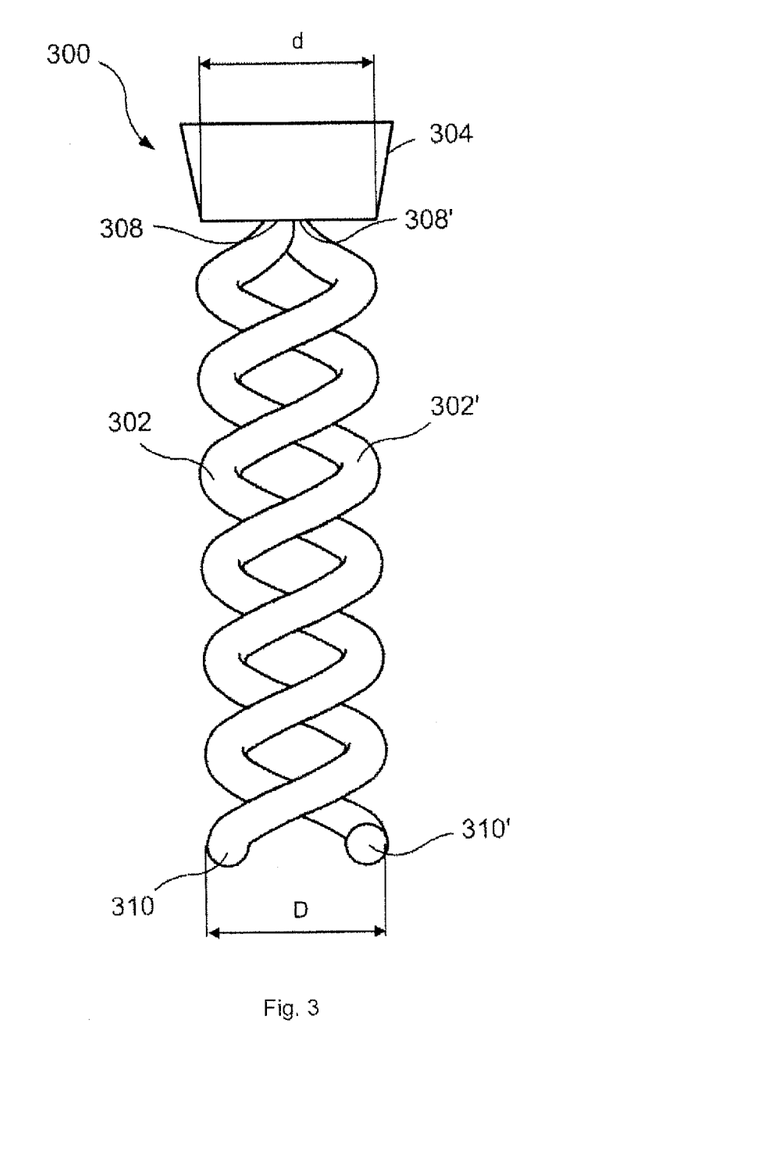
FIG. 3 shows a perspective view of a bone locking spiral according to a third exemplary embodiment of the present invention.

As shown in FIG. 3, a bone screw 300 according to a further embodiment of the present invention comprises a first and a second shaft 302, 302' extending distally from a single head 304. Each of the first and second shafts 302, 302' is formed substantially similarly to the first shaft 102 of FIG. 1. The first and second shaft 302, 302' each has a helically wound structure whereby the first and second shaft 302, 302' have an equal pitch P and whereby the two helix axes coincide. The minimum diameter d of the conical non-threaded head 304 is equal or greater than the outer diameter D of a virtual cylinder enveloping the first and second shaft 302, 302'. Alternatively, one or both of the first and second shafts 302, 302' may be formed with a lumen 212 extending therethrough from respective proximal ends 308, 308' to respective distal ends 310, 310', as described with respect to FIG. 2. As those skilled in the art will understand, the employment of a first and a second shaft 302, 302' provides increased stability to the fractured segments of the bone. For any of the embodiments of the invention, a distal portion of the length of any of the bone spirals may be formed with a reduced degree of rigidity to permit bending thereof. This may reduce the likelihood of sintering of the head of the system when subjected to increased bone resistance, as those skilled in the art will understand. A rigidity of the bone spirals of the present invention can be changed by adjusting any or all of a diameter of predetermined portions of the bone spiral, a pitch and a material of the bone spiral, etc. If a certain rigidity is selected, the bone spiral can compensate for overloads applied by a user via elastic deformation.

Figure 4:
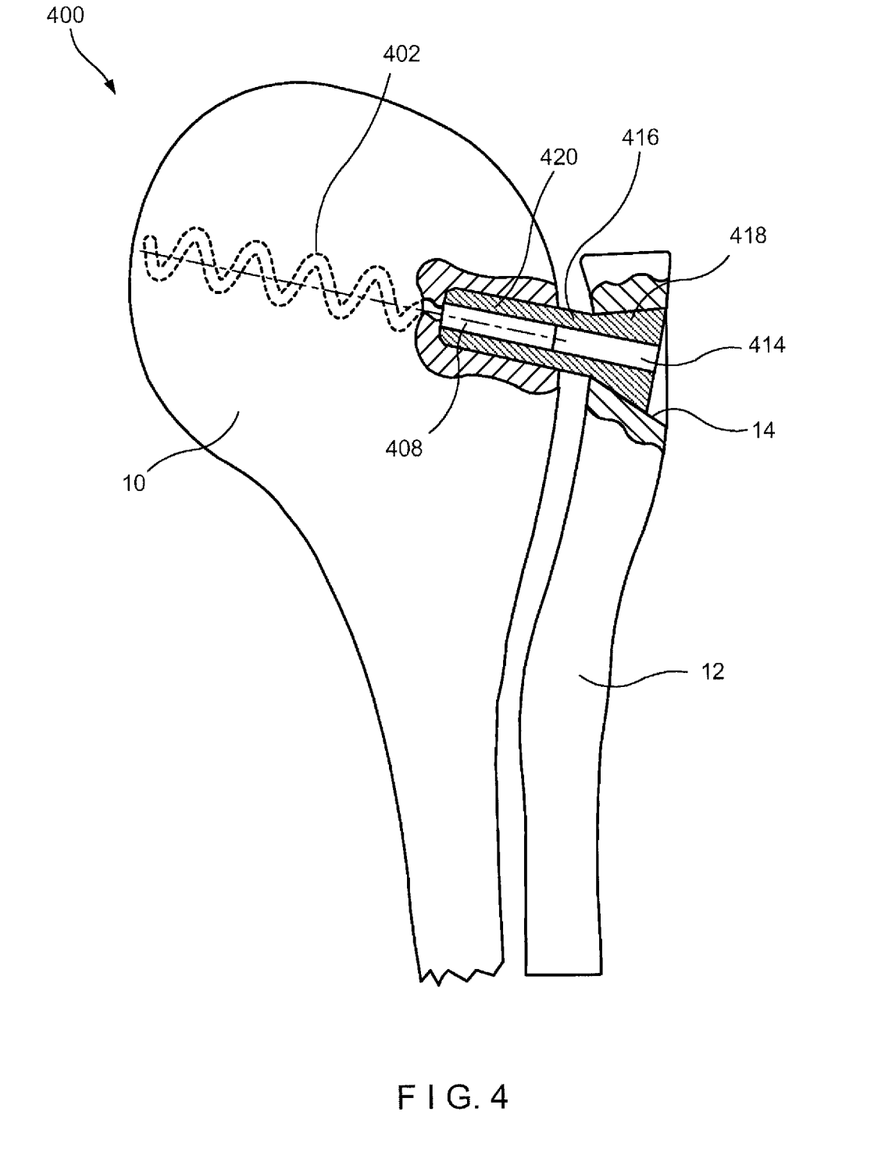
FIG. 4 shows a cross-sectional view of a bone locking spiral according to a fourth exemplary embodiment of the present invention.

FIG. 4 shows a bone screw 400 according to another embodiment of the present invention wherein a first shaft 402 is formed substantially similarly to the first shaft 102 of the bone screw 100 of FIG. 1 with the exception of a head portion thereof. Specifically, a proximal end 408 of the first shaft 402 is fixed to a lumen 414 extending through a cannulated screw 416. The cannulated screw 416 is formed with a proximal head 418 and a shaft 420 extending distally therefrom. The head 418 and shaft 420 may be formed with a threading sized and shaped to lockingly engage threads of an opening 14 formed in a bone plate 12 through which the bone screw 400 is inserted. It is noted however that threading is not an essential requirement of the bone screw 400. A predetermined length of the proximal end 408 of the bone spiral 402 is formed without any spirals to permit insertion and fixation within the lumen 414. The cannulated screw 416 performs the same function as the head 104 of bone screw 100, facilitating gripping and insertion of the first shaft 402 into a target portion of a bone 10. Specifically, the head 418 of the cannulated screw 416 may be formed with slots to permit engagement with a respectively shaped driver, as those skilled in the art will understand.

Figure 6A:
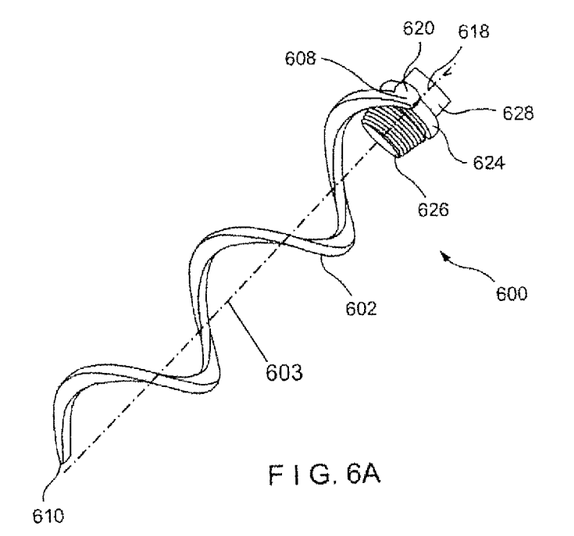
FIG. 6A shows a first perspective view of a bone locking spiral according to a fifth exemplary embodiment of the present invention.
Figure 6B:
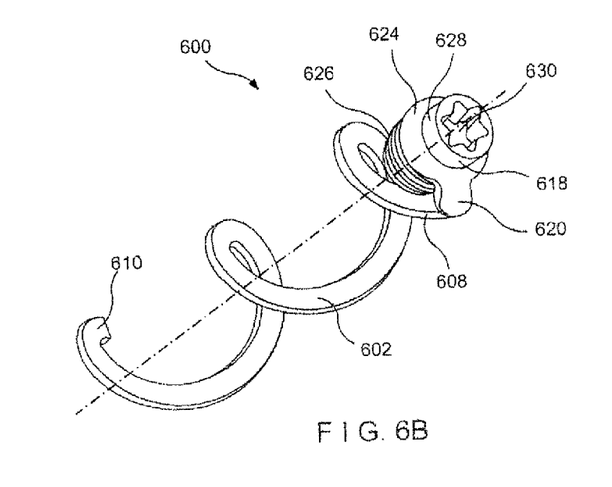
FIG. 6B shows a second perspective view of the bone locking spiral of FIG. 6A.

FIGS. 6A-6B show a bone screw 600 according to another embodiment of the present invention, wherein a first shaft 602 is formed substantially similarly to the first shaft 102 of the bone screw 100 with the exception of a shape of a head 618 thereof and the coupling between the head 618 and the first shaft 602. Specifically, a proximal end 608 of the first shaft 602 is attached to a tab 620 protruding from a circular coupling 624 attached to the head 618. In this embodiment, the coupling 624 is formed as a ring received around the head 618 with a non-threaded portion 628 of the head 618 extending proximally of the coupling 624 and an external thread 626 on the head 618 extending distally thereof. The external thread 626 is conically configured in such a manner that it tapers towards the first shaft 602. The non-threaded portion 628 comprises a recess 630 configured to permit engagement with a distal tip of a driver (not shown). The external thread 626 is configured for screwing into a threaded bone plate hole. The head 618 may be attached to the coupling 624 using any attachment means known in the art and is rotatable relative thereto to permit screwing of the head 618 into the bone plate hole, as will be described in greater detail below. Said first shaft 602 can thus rotate about its axis 603 with respect to said head 618. Specifically, a diameter of the threaded portion 626 is greater than a diameter of the non-threaded portion 628 to prevent the head 618 from sliding proximally out of engagement with the coupling 624.

Figure 6C:
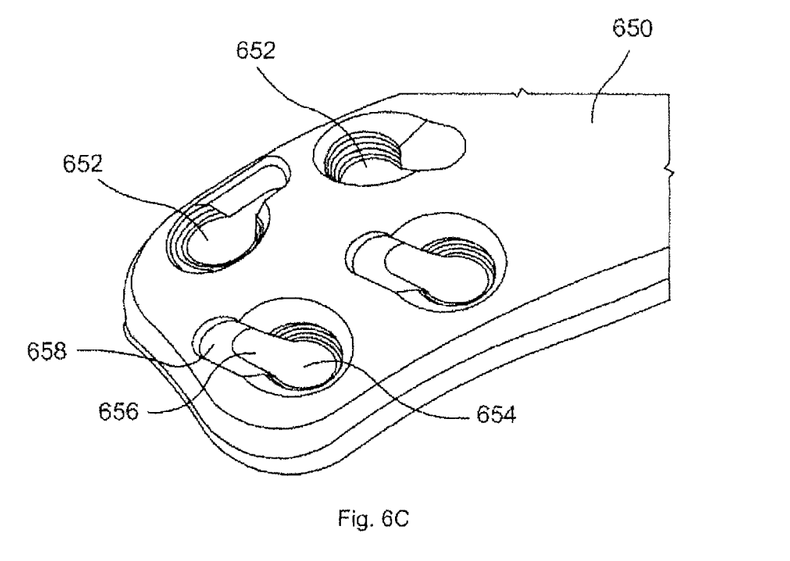
FIG. 6C shows a perspective view of a second exemplary bone plate according to the present invention.

As shown in FIG. 6C, an exemplary bone plate 650 for use with the bone screw 600 including a first shaft 602 comprises a two part plate hole 652. Specifically, the plate hole 652 comprises a first conical portion 654 with an inner thread extending therethrough and configured to threadedly engage the head 618. A second longitudinal portion 656 extends radially outward from the first conical portion 654 to seat the proximal end 608 of the first shaft 602 located adjacent to the head 618. In one embodiment the longitudinal portion 656 has a width large enough to allow the first shaft 602 to be advanced into the bone with the helix steadily passing through the longitudinal portion 656 without displacing the bone plate 650. In one embodiment according to the present invention, a pitch $P_2$ of the shaft 602 is greater than a pitch $P_1$ of the head 618, wherein the ratio $P_2/P_1$ is preferably larger than 7, most preferably larger than 10. In another embodiment the longitudinal portion 656 penetrates through the bone plate 650 with an angle of inclination coinciding with the helix angle of the first shaft 602 so that the first shaft 602 can be advanced into a bone with its helix axis 603 coinciding with the plate hole axis. In a further embodiment the longitudinal portion 656 is configured as a slot with a helical shape wherein the pitch of the slot helix coincides with the pitch P of the first shaft 602. Furthermore, a beveled recess 658 is formed along a periphery of the longitudinal portion 656 to seat the tab 620.

In accordance with an exemplary method according to the present embodiment a first driver (not shown) configured to engage the coupling 624 is used to drive the first shaft 602 into the bone as far as the tab 620 is seated within the longitudinal portion 656 of the plate hole 652. The proximal head 618 which can axially move within the circular coupling 624 has not yet engaged the first conical portion 654. Subsequently, a second driver (not shown) is inserted into the recess 630 to rotatably drive the head 618 into the plate hole 652 as far as the external thread 626 is fixed in the threads of the first conical portion 654.

In accordance with another exemplary method according to the present embodiment, a first driver (not shown) is inserted into the recess 630 to rotatably drive the head 618 into the plate hole 652 until the threaded portion 626 thereof engages threads of the first conical portion 654. Once the head 618 is fixed in the plate hole 652, a second driver (not shown) configured to engage the coupling 624 is used to drive the first shaft 602 into the bone. The second driver (not shown) is also rotatably driven to screw the first shaft 602 through the coupling 624 and straight into the bone until the tab 620 is fully seated within the longitudinal portion 656 of the plate hole 652.

Figure 6D:
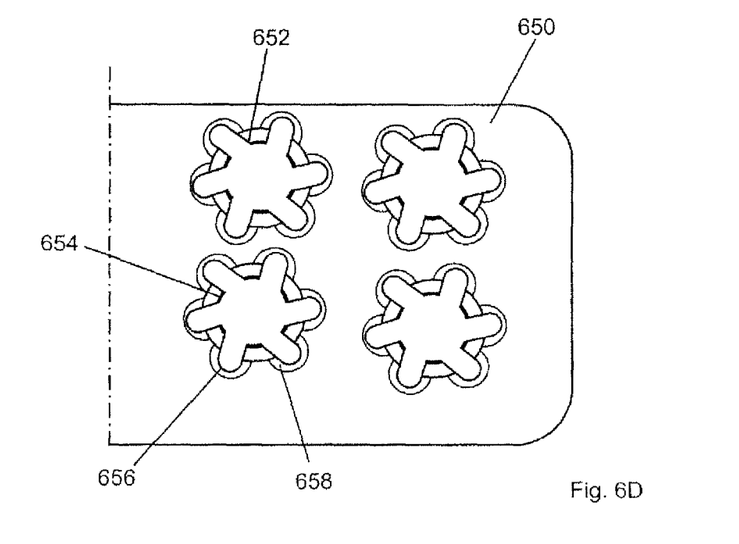
FIG. 6D shows a top view of a third exemplary bone plate according to the present invention.

The plate hole 652 illustrated in FIG. 6D differs from the plate hole 652 of FIG. 6C only therein that it comprises six longitudinal portions 656 which are arranged at equal angles at the periphery of the plate hole 652.

Figure 7A:
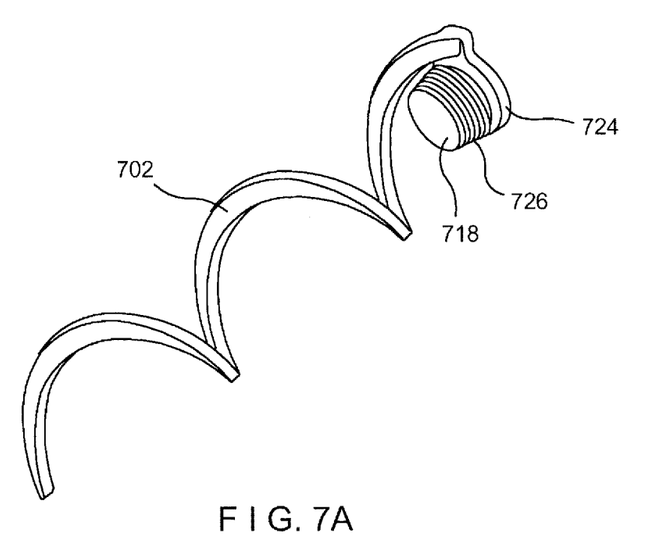
FIG. 7A shows a first perspective view of a bone locking spiral according to a sixth exemplary embodiment of the present invention.
Figure 7B:
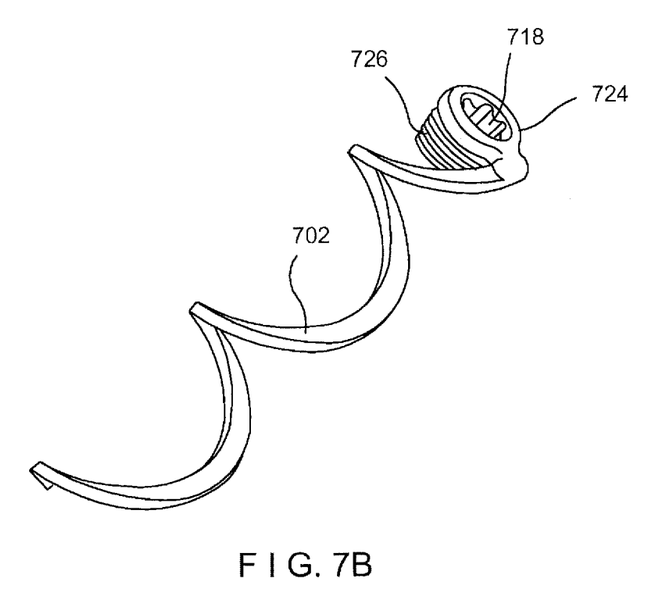
FIG. 7B shows a second perspective view of the bone locking spiral of FIG. 7A.

FIGS. 7A-7B depict another embodiment of the present invention, wherein a first shaft 702 may be formed substantially similarly to the first shaft 602 of FIGS. 6A-6B with the exception of a shape of a head 718 thereof. Specifically, the head 718 is formed substantially similarly to the head 618 but does not protrude proximally from the circular ring of the coupling 724. Rather, the head 718 is connected to the coupling 724 in a manner such that only a threaded portion 726 extends distally therefrom. The head 718 is rotatably attached to the coupling 724 to permit screwing thereof into the bone plate hole 654 in the same manner described above for the first shaft 602. An exemplary method of insertion of the first shaft 702 is substantially similar to the method recited above with respect to FIGS. 6A-6B.

Figure 8A:
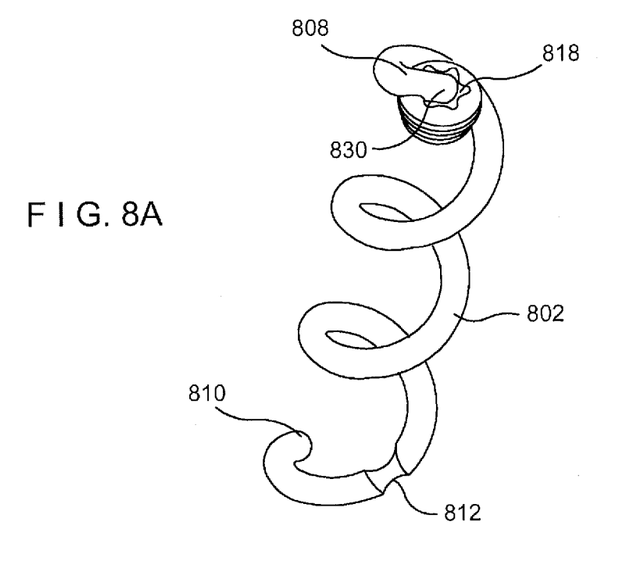
FIG. 8A shows a first perspective view of a bone locking spiral according to a seventh exemplary embodiment of the present invention.
Figure 8B:
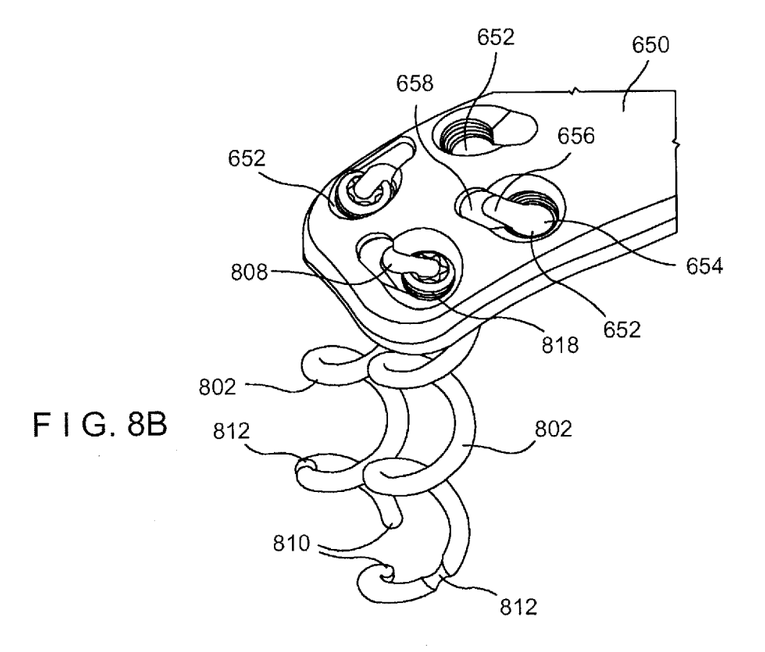
FIG. 8B shows a second perspective view of the bone locking spiral of FIG. 8B.

FIGS. 8A and 8B depict another bone screw with a first shaft 802 according to the present invention formed substantially similarly to the first shaft 602 of FIGS. 6A and 6B with the exception of a shape of a head 818. The head 818 is formed substantially similarly to the head 618 of FIGS. 6A-6B but locks directly to the first shaft 802 without an intervening circular ring therebetween. Specifically, a proximal end 808 of the first shaft 802 spirals around the head 818 and is received within a driver hole 830 located on a proximal surface thereof. An outer wall of the head 818 is completely threaded and configured to be fully inserted into the plate hole 652 in accordance with the method disclosed below.

The first shaft 802 further comprises a notch 812 separated from a distal end 810 by a predetermined distance. The notch 812 is formed by a reduced cross-section of the helically wound thin rod which forms the first shaft 802, defining a bendable region extending distally thereof. Specifically, as those skilled in the art will understand, the mechanical resistance of the notch 812 is lower than other portions of the first shaft 802. Thus, as a mechanical pressure is exerted thereupon during insertion into a target portion of bone, a portion of the first shaft 802 located distally of the notch 812 bends to absorb a portion of the mechanical pressure. This force absorption prevents a perforation of a surface of the target insertion area of the bone by reducing a mechanical pressure exerted thereupon, as those skilled in the art will understand.

According to an exemplary method of the present invention, the first shaft 802 is inserted through the plate hole 654 of the bone plate 650 and screwed into a target portion of bone. Specifically, a first driver (not shown) configured to engage the proximal end 808 is used to drive the first shaft 802 through the second longitudinal portion 656 and into the bone by a predetermined distance so that at least a portion thereof remains externally of the bone. The head 818 is then screwed into the first cylindrical portion 654 by a second driver (not shown) engaging the driver hole 830. Once the head 818 is fixed in the plate hole 652, the first driver (not shown) is used to screw the first shaft 802 further into the bone until the proximal end 808 engages the driver hole 830.

Figure 9A:
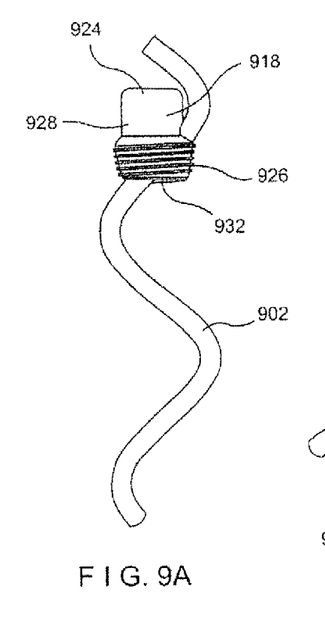
FIG. 9A shows a first perspective view of a bone locking spiral according to an eighth exemplary embodiment of the present invention.
Figure 9B:
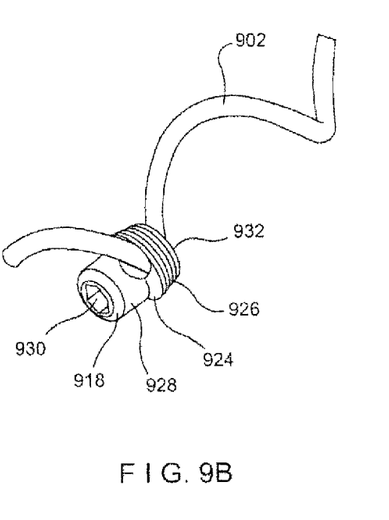
FIG. 9B shows a second perspective view of the bone locking spiral of FIG. 9A.

FIGS. 9A-9B depict another embodiment of the present invention, wherein a head 918 of a first shaft 902 is not attached to a proximal end 908 but is slidable and rotatable therealong. The head 918 is formed substantially similarly to the head 618 of FIGS. 6A-6B and comprises a first threaded portion 926 and a second non-threaded portion 928. A recess 930 configured to permit engagement with a distal tip of a driver (not shown) extends partially through the non-threaded portion 928. The head 918 further comprises a helical through bore 932 extending therethrough at a predetermined angle selected to permit the head 918 to slide along the curves of the first shaft 902 with minimal resistance. Thus, the radial position and the pitch of the helical through bore 932 may be selected to conform to the degree of curvature of the spirals of the first shaft 902. The helical through bore 932 extends from a side wall of the non-threaded portion 928 of the head 918 to a distal face thereof. Preferably, the diameter of the head 904 is greater than the outer diameter of a virtual cylinder enveloping the first shaft 902 so that said first shaft 902 can be advanced into a bone with its helix axis coaxial to the central axis of the head 918.

Figure 9C:
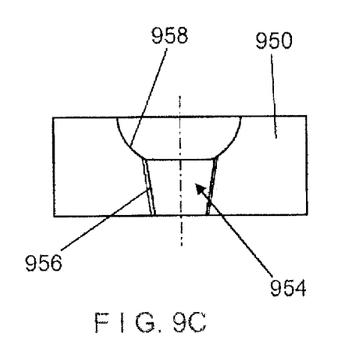
FIG. 9C shows an exemplary bone plate for use with the bone locking spiral of FIG. 9A.

An exemplary plate hole 954 according to the present embodiment comprises a first threaded cylindrical portion 956 adjacent a bottom surface thereof configured to contact the bone in an operative configuration. A rounded tapered portion 958 extends from the threaded portion 956 to a proximal surface of the bone plate 950. In an operative configuration, the first threaded portion 926 of the head 918 is configured to be screwed into the threaded portion 956 of the bone plate hole 954 such that the helical through bore 932 of the non-threaded portion 928 remains within the rounded tapered portion 958 of the plate hole. Thus, the portion of the first shaft 902 extending out of the helical through bore 932 is permitted to rotate during insertion of the head 918 into the bone plate hole 954.

In operation, a guide hole may be predrilled into the target portion of the bone by a sharp instrument, the predrilled guide hole matching a shape of the first shaft 902. The head 918 is screwed into the bone plate hole 954 and tightened to a substantially locked position therein. As described above, in this locked position, the helical through bore 932 remains accessible to a user. The first shaft 902 is then inserted through the helical through bore 932 and is screwed into the bone by a driver (not shown) configured to engage a proximal end thereof. The first shaft 902 may be precut to a length required for a particular procedure or alternatively, may be cut after screwing of a predetermined portion thereof into the bone.

The present invention is directed to a bone screw comprising a proximal head being configured to lockingly engage a bone plate hole and a first substantially helical shaft extending distally from said head along a first substantially helical path, wherein said head and said first shaft are rotatably coupled to each other, so that said shaft can rotate about its axis with respect to said proximal head. In a special embodiment said proximal head includes a driver engaging structure, preferably in the form of a recess formed thereon.

In a further embodiment according to the present invention, the bone screw further comprises a lumen extending through the first shaft from the proximal head to a distal end of the first spiraled shaft and open at both ends thereof.

Another embodiment further comprises a second shaft extending distally from the head with a helix axis coaxial to the helix axis of the first shaft and with a pitch $P_3$ equal to the pitch $P_2$ of a first shaft, wherein a direction of rotation of the second substantially helical path is in the same direction of rotation of the first substantially helical path.

In another embodiment according to the present invention, a diameter of the shaft is a minimum of 0.4 mm, preferably minimum 0.5 min and maximum 3.0 mm, preferably maximum 2.0 mm. The diameter D of the outer virtual cylinder defined by the first shaft is minimum 4.0 mm, preferably minimum 3.0 mm and maximum 30 mm, preferably maximum 10 mm. The shaft further comprises an inner hollow core defining an inner virtual cylinder. Preferably, the difference between the outer virtual cylinder and the inner virtual cylinder is minimum 0.8 mm and maximum 6 mm and the ratio of the diameter of the thin rod to the diameter of said outer virtual cylinder D is preferably minimum 0.1 and preferably maximum 0.25.

In yet another embodiment said head tapers conically towards said first shaft and wherein the cone angle of said head is between 2.8° and 20°. The term cone angle as used herein is the angle enclosed by the peripheral surface of the cone.

The present invention is further directed to a bone screw comprising a proximal head with a conical shape configured to lockingly engage a corresponding conical bone plate hole and a first substantially helical shaft extending distally from the head along a first substantially helical path. In a special embodiment said head and said first shaft are rotatively and axially fixed relative to each other.

In a further embodiment the head of the bone screw has a smooth surface and tapers conically towards said first shaft, preferably with a cone angle between 2.8° and 20°. By means of a conical head having a cone angle in the indicated range, a frictional lock between the head and a corresponding plate hole results by means of which a further rotation of the bone screw relative to the bone plate is prevented. This frictional locking is known as the Morse taper effect.

In another embodiment the proximal head has a minimal diameter d and the first shaft has an outer diameter D and wherein d is equal or greater than D.

In yet another embodiment the head has a helical through bore for slidingly receiving the shaft therein.

In another embodiment said bone fixation system comprises a bone plate comprising first and second plate holes extending therethrough configured to receive bone screws according to invention, the first and second plate holes defining respective hole axes intersecting one another at a point on a side of the bone plate which, when in an operative configuration, faces a bone to which the plate is to be coupled. Further, the system comprises first and second bone screws according to the invention with a shaft each extending along helical paths, the first and second bone screws being dimensioned so that, when received in the first and second plate holes, respectively, the first and second bone screws extend past the point at which the axes of the first and second plate holes intersect.

In again another embodiment the first plate hole is not perpendicular with respect to a longitudinal axis of the bone plate, an angle of the first plate hole relative to the longitudinal axis being chosen to permit insertion of a first bone fixation screw therethrough past a point of intersection with a second bone fixation screw inserted through the second plate hole.

In a further embodiment of said bone fixation system the longitudinal portion is configured as a slot with a helical shape having the same pitch P as the first shaft.

In another embodiment of the bone fixation system the longitudinal portion has a width large enough to allow the first shaft to be advanced into the bone with the helix steadily passing through the longitudinal portion without displacing the bone plate.

In another embodiment the longitudinal portion penetrates through the bone plate with an angle of inclination coinciding with the helix angle of the first shaft so that the first shaft can be advanced into a bone with its helix axis coinciding with the plate hole axis.

It is another object of the present invention to provide a method for bone fixation comprising the steps of positioning a bone plate over a target portion of bone with an upper surface thereof facing away from the bone, inserting a first bone screw according to the invention through a first hole in the bone plate into a first target portion of bone along a first axis, the first bone screw comprising a proximal head and a shaft extending distally from the proximal head along a first substantially helical path, and inserting a second bone screw according to the invention into the second plate hole and into a second target portion of bone so that the first and second bone screws extend past the point at which the axes of the first and second plate holes intersect.

In another embodiment the method further comprises injecting a strengthening element through a lumen extending through the first shaft, wherein the lumen is open at both proximal and distal ends of the shaft.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A bone screw, comprising:
   a proximal head being configured to lockingly engage a bone plate hole; and
   a substantially helical shaft extending distally from the head along a substantially helical path,
   wherein the head and the shaft are rotatably coupled to each other so that the shaft can rotate about a central longitudinal axis thereof with respect to the head and wherein the head is rotatably coupled to a circular coupling attached to the shaft.

2. The bone screw according to claim 1, wherein the head includes a driver engaging structure in the form of a recess formed thereon.

3. The bone screw according to claim 1, wherein the head comprises an external thread having a pitch $P_1$ for lockingly engage the bone plate hole, and wherein the shaft is formed in a helical shape having the pitch $P_2$.

4. The bone screw according to claim 3, wherein the pitch $P_2$ of the shaft is greater than the pitch $P_1$ of the external thread and wherein the ratio $P_2/P_1$ is larger than 7.

5. The bone screw according to claim 4, wherein the ratio $P_2/P_1$, is larger than 10.

6. The bone screw according to claim 3, wherein the external thread is a multiple thread.

7. The bone screw according to claim 3, wherein the external thread is a double thread.

8. The bone screw according to claim 1, wherein the circular coupling includes a tab extending radially therefrom to engage a respectively sized portion of the bone plate hole.

9. The bone screw according to claim 1, wherein the circular coupling includes a driver engaging structure formed thereon.

10. The bone screw according to claim 1, wherein the head and the shaft are coupled to each other in an axially fixed manner.

11. The bone screw according to claim 1, wherein a coupling between the head and the shaft permits an axial relative movement between 0.5 mm. and 3.0 mm.

12. The bone screw according to claim 1, wherein the head has a helical through bore configured to slidingly receive the shaft therein.

13. The bone screw according to claim 1, wherein a cross-sectional shape of the shaft is one of circular, oval, triangular, rectangular and hexagonal.

14. The bone screw according to claim 1, wherein the shaft has the form of a helically wound thin rod.

15. A bone screw, comprising:
- a proximal head being configured to lockingly engage a bone plate hole; and
- a substantially helical shaft extending distally from the head along a substantially helical path,
- wherein the head and the shaft are rotatably coupled to each other so that the shaft can rotate about a central longitudinal axis thereof with respect to the head and wherein a distal portion of the shaft has a rigidity less than that of a proximal portion thereof to facilitate bending during insertion.

16. The bone screw according to claim 15, wherein the shaft comprises a notch located in a distal portion.

17. A bone screw, comprising:
- a proximal head being configured to lockingly engage a bone plate hole; and
- a substantially helical shaft extending distally from head along a substantially helical path,
- wherein the head and the shaft are rotatably coupled to each other so that the shaft can rotate about a central longitudinal axis thereof with respect to the head and wherein the head tapers conically towards the shaft at an angle between 2.8° and 20°.

* * * * *

UNITED STATES PATENT AND TRADEMARK OFFICE
CERTIFICATE OF CORRECTION

PATENT NO. : 9,642,662 B2
APPLICATION NO. : 12/752748
DATED : May 9, 2017
INVENTOR(S) : Appenzeller et al.

Page 1 of 1

It is certified that error appears in the above-identified patent and that said Letters Patent is hereby corrected as shown below:

Claim 3, Column 10, Line 44:
"comprises an external thread having a pitch $P_1$ for lockingly" should read "comprises an external thread having a pitch $P_1$ to lockingly".

Claim 17, Column 11, Line 25:
"a substantially helical shaft extending distally from head" should read "a substantially helical shaft extending distally from the head".

Signed and Sealed this
Twenty-fourth Day of July, 2018

Andrei Iancu
*Director of the United States Patent and Trademark Office*